United States Patent [19]

Ishii et al.

[11] Patent Number: 5,244,661

[45] Date of Patent: Sep. 14, 1993

[54] PROCESS FOR PRODUCING A POLYENE ANTIBIOTIC

[75] Inventors: Koichi Ishii; Shigeyoshi Miyashiro, both of Kawasaki, Japan

[73] Assignee: Ajinomoto Company, Inc., Tokyo, Japan

[21] Appl. No.: 514,951

[22] Filed: Apr. 26, 1990

[30] Foreign Application Priority Data

Apr. 26, 1989 [JP] Japan .................................. 1-106167
Sep. 7, 1989 [JP] Japan .................................. 1-230357
Mar. 7, 1990 [JP] Japan .................................. 2-53807

[51] Int. Cl.$^5$ ............................................. A61K 35/74
[52] U.S. Cl. ................................................... 424/123
[58] Field of Search ........................................ 424/123

[56] References Cited

U.S. PATENT DOCUMENTS 3,773,925 11/1973 Benzzese et al. ................... 424/122
3,793,448 2/1974 Schaffner et al. ................... 424/119
4,642,318 2/1987 Wolff .................................. 514/560

OTHER PUBLICATIONS

Canadian Journal of Chemistry, vol. 63, No. 1, Jan. 1985, pp. 77-85; N. O. Petersen: "Intramolecular fluorescence energy transfer in nitrobenzoxadiazole derivatives of polyene antibodies".

*Primary Examiner*—Jerome D. Goldberg
*Attorney, Agent, or Firm*—Oblon, Spivak, McClelland, Maier & Neustadt

[57] ABSTRACT

By irradiating a polyene antibiotic having a cis-type polyene structure with long wavelength ultraviolet light, it is possible to prepare the corresponding antibiotic having a trans-type polyene structure in high yield in a simple manner. Such antibiotics having a trans-type polyene structure exhibit strong antimicrobial activities and are useful as drugs for humans or animals.

4 Claims, 3 Drawing Sheets

PROCESS FOR PRODUCING A POLYENE ANTIBIOTIC

BACKGROUND OF THE INVENTION

1. Field of the Invention

The present invention relates to a process for efficiently producing trans-type polyene antibiotics by irradiation with ultraviolet light, and the antibiotics produced by such a process. The substances obtained by the process of the present invention have antifungal activity and can thus be used as medical drugs, animal drugs, etc.

2. Discussion of the Background

As a polyene antibiotic having a cis-type polyene structure, partricin is known (*J. Antibiotics*, vol. 35, 997 (1982)). The stereo structure of polyenes, either trans-type or cis-type, is determined at the stage where these antibiotics are produced by microorganisms in fermentation solutions; and at present, it is extremely difficult to artificially change this stereo structure. However, it is known that when a diluted solution of partricin which is a cis-type polyene antibiotic is exposed to light, the maximum absorption wavelength in the ultraviolet region is shifted by 4 nm to the longer wavelength region. It is considered that this wavelength shift occurs because cis-type partricin is changed to trans-type (U.S. Pat. No. 3,773,925; issued Nov. 20, 1973).

In general, polyenes are very unstable to exposure to light. For example, as described in the literature supra, even though a partricin solution is simply exposed to light, conversion into trans-type occurs and at the same time, the formed trans-type compound is decomposed so that the product is finally completely decomposed. Thus, any case where the trans-type compound obtained by the photoreaction is isolated as a chemically pure substance is unknown. In addition, no processes which are utilized for the industrial production of trans-type antibiotics by exposure to light are known. Thus, there remains a need for a process for efficiently converting cis-type polyene antibiotics into trans-type polyene antibiotics in a simple manner.

SUMMARY OF THE INVENTION

Accordingly, one object of this invention is to provide a novel method for producing a trans-type polyene antibiotic.

It is another object of the present invention to provide trans-type polyene antibiotics.

These and other objects, which will become apparent during the following detailed description, have been achieved by the inventors' discovery that by irradiating a solution of a cis-type polyene antibiotic with ultraviolet rays in the long wavelength region the cis-type polyene antibiotic may be efficiently converted to a trans-type polyene antibiotic. That is, the present invention relates to a process for producing polyene antibiotics having a trans-type polyene structure which comprises irradiating a solution of polyene antibiotics having a cis-type polyene structure with light containing ultraviolet rays in the long wavelength region, and the antibiotic produced by such irradiation.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
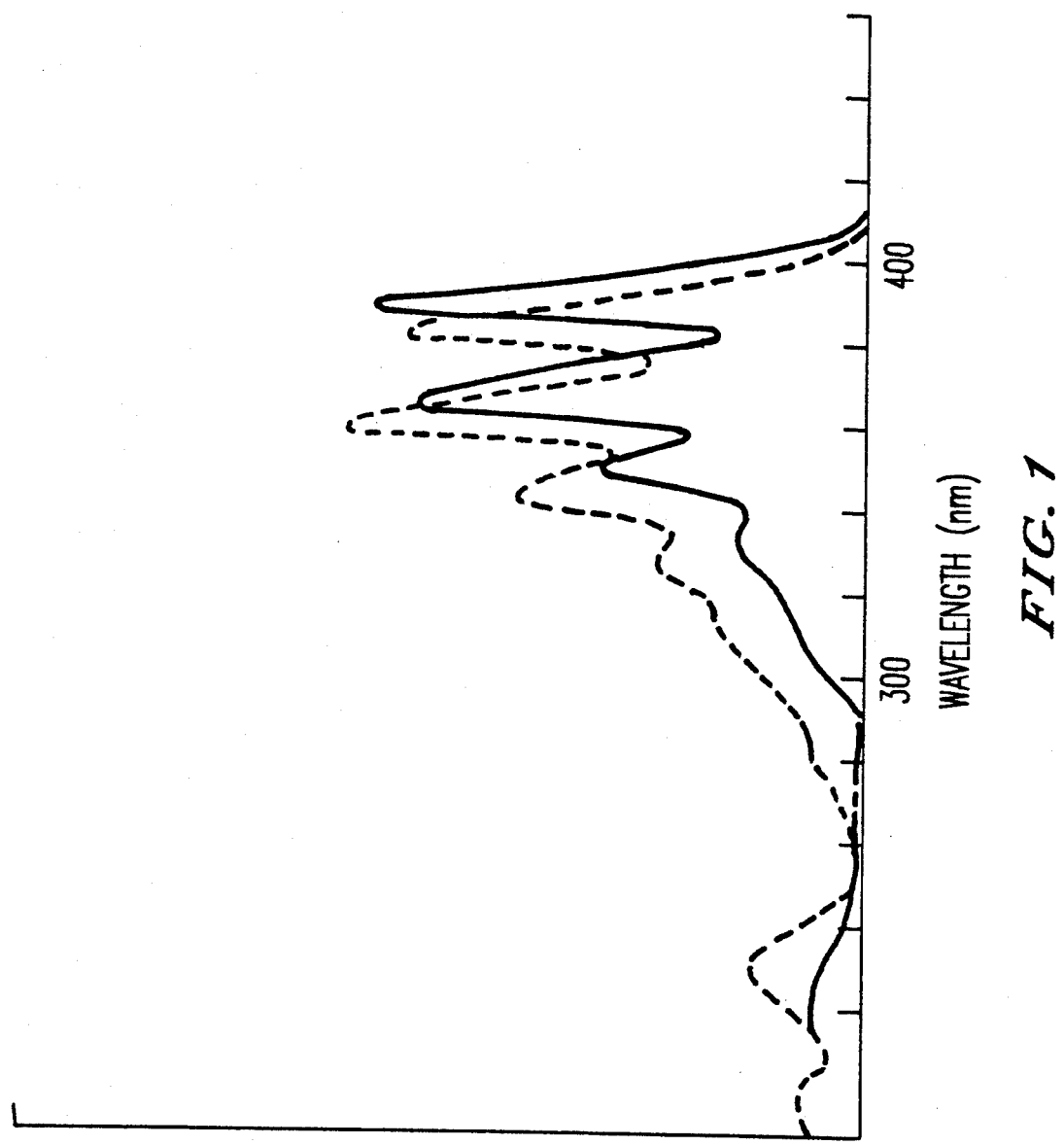
FIG. 1 illustrates the UV spectra of the trans isomer of partricin B (solid line) and partricin B (broken line)

Representative of polyene antibiotics having a cis-type polyene structure, there are partricin (*J. Antibiotics*, vol. 35 (8), 997–1012 (1982), U.S. Pat. No. 3,773,925), partricin methyl ester (Japanese Patent Publication No. 55-50960), ayfactin (*Antibiot. & Chemoth.* Vol. 8, pp. 491–495 (1958)), hamycin (*Hindustan Antibiot. Bull.*, vol. 3, pp. 136–138 (1961)), trichomycin, (*J. Antibiotics*, vol. 5, pp. 564–566 (1952)), aureofungin (*Hindustan Antibiot. Bull.*, vol. 6, pp. 108–111 (1964)), candimycin (*J. Antibiotics*, Ser. B, 7, pp. 168–170 (1954)), DJ-400 (*Tetrahedron*, Vol. 26, pp. 2191–2198 (1970)), candicidin (*Mycologia*, vol. 45, pp. 155–171 (1953)), levorin (*Chemotherapia*, vol. 10, pp. 176–194 (1965)), vacidim A (*J. Antibiotics*. vol. 42, pp. 1631–1638 (1989)), gedamycin (*J. Antibiotics*, Ser. B, 9, pp. 79–80 (1956)), etc. These antibiotics may be purified products or may be in a state of crude products which contain impurities.

Solvents for dissolving the polyene antibiotics are desirably hydrophilic organic solvents such as methanol, ethanol, acetonitrile, dimethylformamide, dimethylacetamide, dimethylsulfoxide, etc.; and water-containing organic solvents containing at least 30% by weight of these organic solvents. An alcohol aqueous solution containing approximately 5 to 30% by weight of water, especially aqueous methanol solution, is preferred. It is more preferred to add salts to the solution. The salt may be sodium chloride, sodium acetate, ammonium acetate, etc. but the type of salt is not limited. The concentration of the salt may be 5 mM or more, preferably 5 to 1000 mM, more preferably 10 mM to 200 mM. It is appropriate that the concentration of the polyene antibiotic be approximately 1 to 1000 mg/l. When the solvent is a water-containing solvent, it is preferred to adjust the pH to below 10, especially 5.5 to 9, in order to minimize the decomposition of the produced trans-type polyene antibiotics.

The wavelength of the ultraviolet rays used in the present invention is appropriately 300 to 400 nm. Light of a longer wavelength region may also be used together with wavelengths of from 300 to 400 nm, since such a light does not cause isomerization. On the other hand, it is preferred not to use light of a wavelength region shorter than 300 nm, because such light causes decomposition of polyene antibiotics. That is, it is preferred to carry out the irradiation with light that is substantially free of light having a wavelength shorter than 300 nm. The decomposition products are considered to be substances in which the polyene chromophore formed by cleavage of the polyene bond is ring-opened. The quantum efficiency of irradiation at about 300 nm is approximately $2 \times 10^{-2}$. The term quantum efficiency refers to the ratio of reacted molecules to photons absorbed.

As the light source, a variety of light sources which can be used industrially are suitable. For example, natural light, a daylight fluorescent lamp, a cold white fluorescent light, a medium near-ultraviolet ray lamp, a long wavelength ultraviolet ray lamp, etc. may be used. Of these, a long wavelength ultraviolet ray lamp emitting a single ultraviolet ray at 365 nm is particularly preferred. The time period for irradiation is adjusted in such a manner that conversion into the trans-type antibiotic is sufficient for the required purposes.

Purification of the trans-type compound can be performed, e.g., by reverse phase chromatography which is a conventional method for isolation and purification of polyene antibiotics. For example, column chromatography using Capcell pak ODS column (manufactured by Shiseido Co., Ltd.), LRP-1 (manufactured by Whatmann Co., Ltd., carrier for C-18 reverse phase chromatography), etc. is effective.

Thus, by irradiating a solution of a polyene antibiotic having a cis-type polyene structure with light containing ultraviolet rays in the long wavelength region, according to the present invention, the cis-type polyene antibiotic can be excited and isomerized to the trans-type polyene antibiotic. Accordingly, the trans-type antibiotic may be obtained in high yield and in substantially pure form.

The polyene antibiotics having a trans-type polyene structure possess excellent antimicrobial activities and thus, are useful for the treatment or prevention of infections in humans or animals.

Other features of the present invention will become apparent in the course of the following descriptions of exemplary embodiments which are given for illustration of the invention and are not intended to be limiting thereof.

EXAMPLES

Example 1

One kiloliter of medium having the composition shown in Table 1 was sterilized by heating and charged into a fermenter. Partricin B-producing *Streptomyces arenae* (FERM P-8099, FERM BP-1537) was inoculated on the medium followed by culturing at 28° C. for 3 days.

TABLE 1

| | |
|---|---|
| Glucose | 6% |
| Sodium glutamate | 4% |
| Yeast extract | 0.2% |
| Polypeptone | 0.2% |
| Magnesium sulfate 7 hydrate | 0.01% |
| Sodium chloride | 0.5% |
| Water | 89.09% |

After culturing, mycelia were collected by centrifugation and 100 l of methanol was added thereto. After the pH was adjusted to 6.0 with acetic acid, the system was allowed to stand at room temperature for 24 hours. Then, filtration was performed and 100 l of the resulting filtrate was concentrated to 10 l under reduced pressure. The precipitates were collected by centrifugation and freeze dried to give 200 g of crude partricin B (purity 65%)

Crude partricin B, 100 g, was purified by reverse phase partition HPLC (Capcell pak ODS column, manufactured by Shiseido Co., Ltd.) to give 80 g of purified dry partricin B (purity, 98%). The physicochemical properties of purified partricin B were examined and were identical with those of partricin B (*J. Antibiotics*, vol. 35, 997 (1982)) in molecular weight of 1112 (determined by FABMS), Rf value of 0.34 in thin layer chromatogram [manufactured by Whatmann Co., Ltd., PLKC18F TLC plate, developing solvent: $CH_3CN$-50 mM $NH_4OAc$ (pH 9.0)=45:55]; retention time of 5.10 minutes in HPLC [column: YMC AM-312$\phi$4.5 ×150 mm, solvent: $CH_3CN$-50 mM $NH_4OAc$ (pH 5.5)=4.5 : 5.5, flow rate: 1.00 ml/min], UV absorption spectrum (measured in MeOH, shown by broken line in FIG. 1) and IR spectrum, giving a single spot by TLC and a single peak by HPLC.

The purified partricin B prepared by the above method was dissolved in 90% methanol solution (50 mM ammonium acetate was added and the pH was adjusted to 5.8 with acetic acid) in a concentration of 40 mg/l. One liter of this solution was charged into a stainless vat in a solution depth of 1 cm in a dark room. While gently stirring, the solution was irradiated with two long wavelength ultraviolet ray lamps (wavelength of 365 nm, UV lamp of 8 W, intensity of 410 $\mu w/cm^2$) at a distance of 12.7 cm for 20 minutes. The irradiated solution was concentrated to 100 ml under reduced pressure and the formed precipitates were collected by centrifugation. The precipitates were washed twice with 25 ml of water and dissolved in a small quantity of tetrahydrofuran solution. The resulting solution was applied to LRP-1 reverse phase chromatography column, which was eluted with a mixture of acetonitrile:0.05M ammonium acetate (pH 9.0)=4.5:5.5. Absorbance was measured at 360 nm and the eluted fractions of the product by irradiation with ultraviolet rays (hereafter referred to as UVP-A) were collected. After concentrating under reduced pressure, the residue was allowed to stand in a refrigerator overnight. The next day, the precipitated yellow crystals of UVP-A were collected by centrifugation and dried to give 30 mg of purified UVP-A. The physicochemical properties of UVP-A are as follows.

(1) Elemental analysis: C: 62.85%, H: 7.66%, N: 2.55%
(2) Molecular weight: 1112 (determined by FABMS)
(3) Optical rotation: $[\alpha]_D^{26}$: +335° (c=0.1% dimethyl sulfoxide)
(4) UV spectrum: as shown in FIG. 1 (measured in MEOH, shown by solid line)
(5) Rf value: 0.26 [manufactured by Whatmann Co., Ltd., PLKC18F TLC plate, developing solvent: $CH_3CN$-50 mM $NH_4OAc$ (pH 9.0)=45 : 55]
(6) Retention time of HPLC: 8.00 minutes [column: YMC AM-132 $\phi$ 4.5×150 mm, solvent: $CH_3CN$-50 mM $NH_4OAc$ (pH 5.5)=4.5:5.5, flow rate: 1.00 ml/min]

Figure 2:
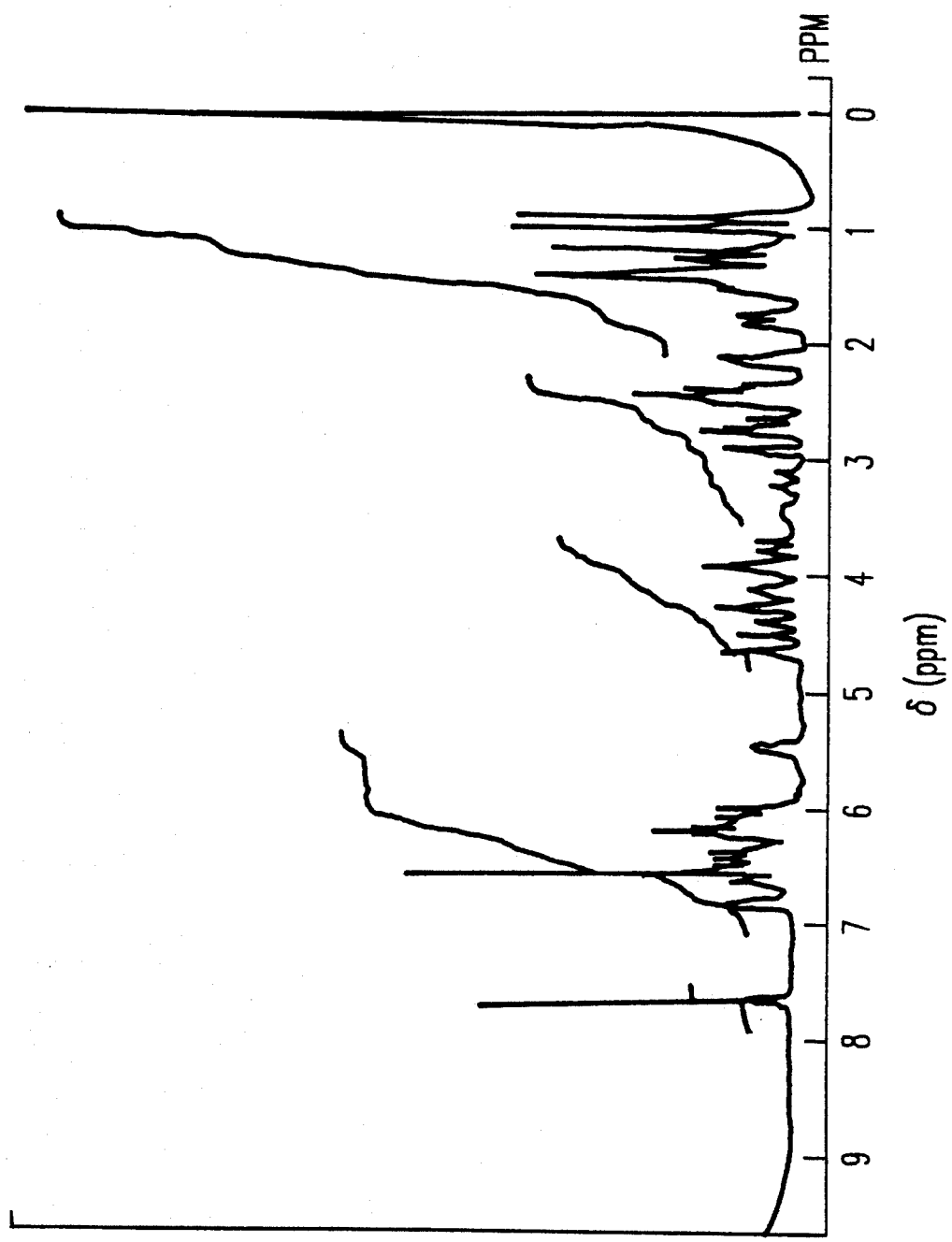
FIG. 2 illustrates the $^1H$ NMR spectrum of partricin B in DMSO-$d_6$.
Figure 3:
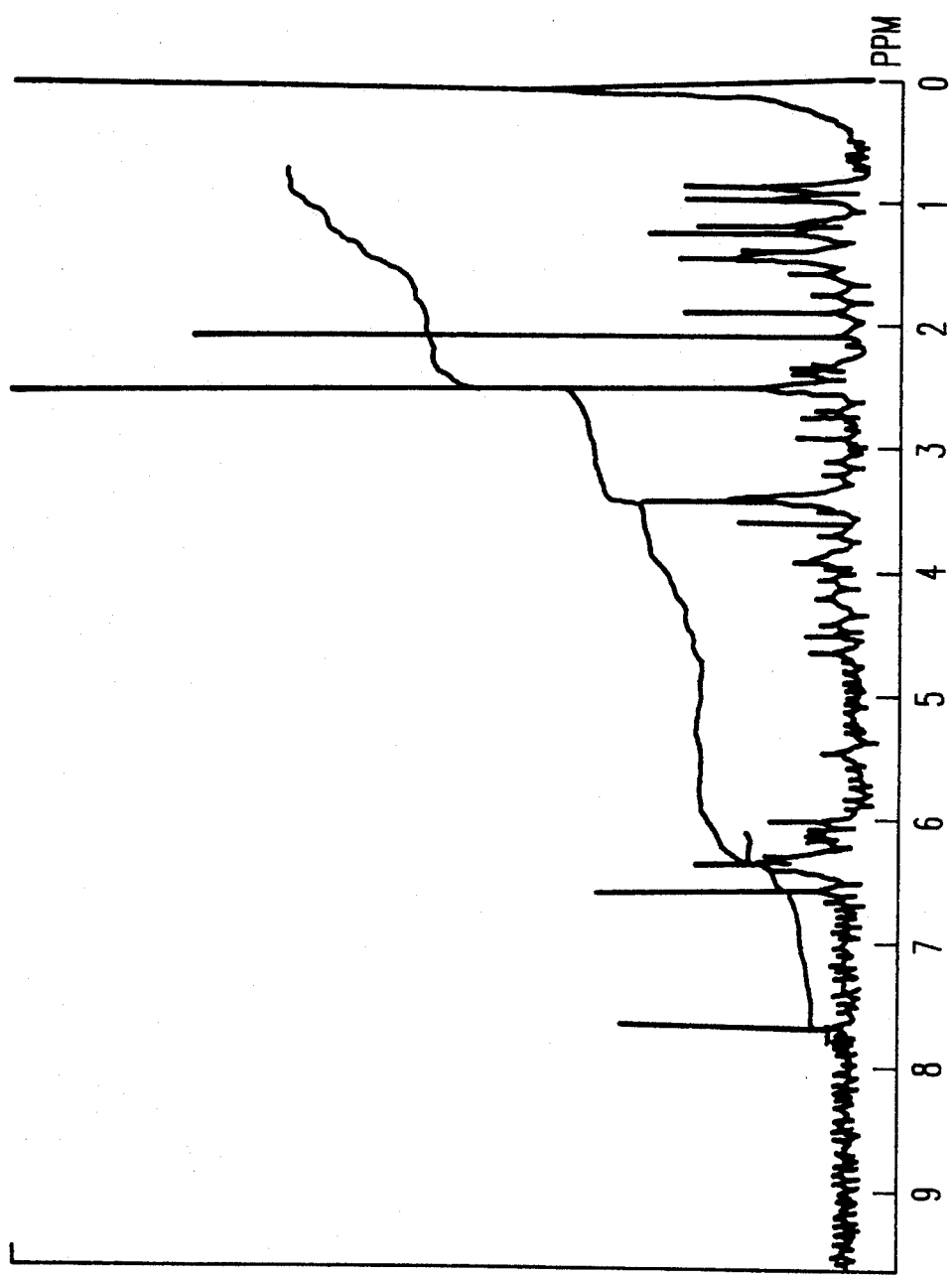
FIG. 3 illustrates the $^1H$ NMR spectrum of UVP-A in DMSO-$d_6$.

A comparison of the physicochemical properties of partricin B and UVP-A are shown in Table 2. As shown in Table 2, the molecular weight is identical, and the UV spectra and optical rotations are different, indicating that UVP-A is a trans-type isomer of partricin B. When the $^1H$-NMR data of both antibiotics (FIG. 2 and FIG. 3) are compared, they are nearly identical as a whole. A difference is noted between 5.5 and 6.5 ppm, and this difference indicates a difference in the structure of the polyene structure in both compounds.

TABLE 2

| Physicochemical Property | Partricin B | UVP-A |
|---|---|---|
| Molecular weight | 1112 | 1112 |
| $UV\lambda_{max}^{MeOH}(\epsilon)$ | 400 (87,558) | 404 (150,380) |
| | 378 (100,425) | 380 (130,700) |
| | 358 (73,392) | 361 (82,900) |

TABLE 2-continued

| Physicochemical Property | Partricin B | UVP-A |
|---|---|---|
| $[\alpha]_D^{26}$ | +114° | +335° |

As shown in Table 3, UVP-A has a potent antibacterial activity as compared to partricin B. The minimum growth inhibitory concentration (MIC) against *Candida albicans* was 0.005 μg/ml.

TABLE 3

| | MIC (μg/ml) | |
|---|---|---|
| Strain | Partricin B | UVP-A |
| *Candida albicans* ATCC 10231 | 0.04 | 0.005 |
| *Saccharomyces ubran* ATCC 9080 | 0.04 | 0.005 |

Example 2

Purified partricin B was prepared in a manner similar to that described in Example 1 and dissolved in a concentration of 40 mg/l in a solvent of 90% methyl alcohol aqueous solution which contained 50 mM ammonium acetate. One liter each of the solution was irradiated with light having various wavelengths for 20 minutes. The produced UVP-A was isolated and its quantity was determined. The results are shown in Table 4.

TABLE 4

| Wavelength (nm) | Quantity of UVP-A Formed (mg) |
|---|---|
| 225 | 0 |
| 320 | 7 |
| 365 | 28 |
| 400 | 8 |
| 436 | 0 |
| 580 | 0 |

Example 3

Partricin B was irradiated with light using various light sources in a manner similar to Example 2. As the result, the amount of UVP-A formed is as shown in Table 5.

TABLE 5

| | Quantity of UVP-A Formed (mg) Time for Irradiation | |
|---|---|---|
| Light Source | 20 Minutes | 72 Hours |
| Natural light (sunlight) | 12 | * |
| Daylight fluorescent lamp | 0 | 12 |
| Cold white fluorescent lamp | 0 | 12 |
| Medium near-UV fluorescent lamp | 12 | * |
| Long wavelength UV lamp | 28 | * |

*not measured

Example 4

One liter (containing 50 mg of partricin B) of the methanol extract of the cultured cells of *Streptomyces arenae* obtained in a manner similar to that described in Example 1 was irradiated with ultraviolet rays in a manner similar to Example 1. UVP-A was isolated from the irradiated solution to give 20 mg of the purified product as a dry product.

Example 5

One liter of 40 mg/l partricin B solutions dissolved in various solvents in a manner similar to Example 1 and Example 2 was irradiated with two long wavelength ultraviolet ray lamps (wavelength of 365 nm, UV lamp of 8 W, intensity of 410 μw/cm²) at a distance of 12.7 cm for 20 minutes. The produced UVP-A was isolated and its quantity was determined. The results are shown in Table 6.

TABLE 6

| Solvent | Quantity of UVP-A Produced (mg) |
|---|---|
| Water | <5 |
| 90% Methanol aqueous solution | 28 |
| 80% Methanol aqueous solution | 26 |
| 90% Ethanol aqueous solution | 25 |
| Methanol | <5 |
| Ethanol | <5 |
| Acetonitrile | <5 |
| Dimethylformamide | 8 |
| Dimethylacetamide | 8 |
| Dimethylsulfoxide | 8 |

Example 6

In 250 ml of dimethylsulfoxide was dissolved 30 g of partricin B prepared in a manner similar to that described in Example 1. While slowly stirring at room temperature, 200 ml of a 2% ethereal solution of diazomethane was added to the solution. Then, the mixture was allowed to stand overnight in such a state that light was shielded. Ether was added to the mixture to precipitate the product. The precipitates were recovered by filtration. After washing with ether, the precipitates were dried in vacuum. The resulting crude partricin B methyl ester was purified by the method described in Japanese Patent Publication No. 55-50960 to give 5 mg of the purified ester as a dry product. This compound showed the following physicochemical properties and was identified as partricin B methyl ester (substance described in Japanese Patent Publication No. 55-50960).

(1) Appearance: yellow powder
(2) Molecular weight: 1126 (determined by FABMS)
(3) Molecular formula: $C_{59}H_{86}N_2O_{19}$
(4) UVmax: 401, 378, 359, 340 nm Furthermore, absorption at 1715 cm$^{-1}$ derived from C=O of the methyl ester was observed in the IR absorption spectrum, and the characteristic peak of the methyl group at 3.25 ppm due to the presence of the ester group was noted in the $^1$H-NMR spectrum.

Example 7

Crude partricin B methyl ester, 5 mg, obtained in a manner similar to that described in Example 6 was dissolved in 1 liter of a 90% MeOH solution (50 mM ammonium acetate was added and the pH was adjusted to 6.0 with acetic acid). The solution was irradiated with ultraviolet rays of 365 nm, using a long wavelength ultraviolet ray lamp in a manner similar to that of Example 1. The irradiated solution was concentrated and the formed precipitates were recovered by centrifugation. Then the precipitates were purified by high performance liquid chromatography (HPLC, flow rate of 1.0 ml/min) using Novaback C18 (product by Waters Co., Ltd.) as a carrier, 10 mM ammonium acetate buffer (pH 8.5) containing 65% acetonitrile as a moving phase and a UV (405 nm) detector as a detector. The peak eluted at 7.5 minutes was recovered and concentrated in vacuum. The formed precipitates were collected by centrifugation and dried. The dry product was obtained in a 1.5 mg yield. The purified product (referred to as UVP-B) showed the following properties:
(1) Appearance: yellow powder
(2) Molecular weight: 1126 (determined by FABMS)
(3) Molecular formula: $C_{59}H_{86}N_2O_{19}$
(4) UVmax: 405, 382, 344 nm When partricin B methyl ester is compared with UVP-B in physicochemical properties, the molecular weight and molecular formula are identical, but the maximum wavelength of UV absorption is different, indicating that partricin B methyl ester having a cis-type polyene structure has been converted to UVP-B having a trans-type polyene structure. Furthermore, the minimum growth inhibitory concentration (MIC) of UVP-B against Candida albicans ATCC 10231 was 0.39 μg/ml. Thus, UVP-B possesses a more potent activity than partricin B methyl ester (MIC=0.52).

Example 8

One liter of a 95% ethanol aqueous solution of 40 mg/l of partricin B, to which 50 mM of various salts were added and the pH of which had been adjusted to 8 in a manner similar to that of Example 1 and Example 2, was irradiated with two long wavelength ultraviolet ray lamps (wavelength of 365 nm, UV lamp of 8 W, intensity of 410 μw/cm$^2$) at a distance of 2.7 cm for 60 minutes. The produced UVP-A was isolated, and its quantity was determined. The results are shown in Table 7.

TABLE 7

| Salt | Quantity of UVP-A Produced (mg) |
| --- | --- |
| No addition | 0.4 |
| Ammonium acetate | 39 |
| Potassium acetate | 36 |
| Sodium acetate | 35 |
| Sodium chloride | 32 |
| Ammonium chloride | 32 |

Example 9

One milliliter of a 95% ethanol aqueous solution of 20 mg/l of partricin B, to which 50 mM of ammonium acetate was added and the pH of which had been adjusted to 8 in a manner similar to that of Example 1 and Example 2, was irradiated with light having a wavelength of 302, 320, 365 or 405 nm for 30 minutes, using a fluorescent spectrophotometer. The amount of the UVP-A produced was quantitatively determined. The quantitative determination was performed by reverse phase column chromatography YMC pack AM-312 (manufactured by Yamamura Chemical Research Institute), using as an eluting solution acetonitrile : 50 mM ammonium acetate (pH 5.5)=4.5:5.5, whereby a quantum efficiency was determined. The results are shown in Table 8. The irradiation described above was carried out under such conditions that 100% of the partricin B was converted into UVP-A and the produced UVP-A was not decomposed.

TABLE 8

| Wavelength | Quantum Efficiency |
| --- | --- |
| 302 nm | $2.576 \times 10^{-2}$ |
| 320 nm | $1.692 \times 10^{-2}$ |
| 365 nm | $3.809 \times 10^{-3}$ |
| 405 nm | $2.024 \times 10^{-3}$ |

As shown by the above-described examples, according to the process of the present invention, polyene antibiotics having a trans-type polyene structure which can be used as medical drugs for humans or animal drugs can be prepared from polyene antibiotics having a cis-type polyene structure, which have a strong toxicity as medical drugs for humans or animal drugs, in a simple apparatus and operation, in a high yield, by converting the cis-type polyene antibiotics into the trans-type polyene antibiotics.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for preparing the trans isomer of polyene antibiotic, comprising irradiating a solution of a cis-type isomer of a polyene antibiotic with ultraviolet light having a wavelength of 300 nm to 400 nm, to obtain said trans-type isomer of said polyene antibiotic, wherein said polyene antibiotic is partricin or partricin methyl ester, wherein the time period for irradiation is sufficient for conversion into said trans isomer, wherein said solution contains a salt selected from the group consisting of ammonium acetate, potassium acetate, sodium acetate, sodium chloride, and ammonium chloride, wherein said salt is present in a concentration of 5 nM to 1000 nM and wherein said polyene antibiotic is present in a concentration of approximately 1 mg/l to 1000 mg/l.

2. The process of claim 1, wherein said cis-type isomer of said polyene antibiotic is partricin.

3. The process of claim 1, wherein said cis-type isomer of said polyene antibiotic is partricin methyl ester.

4. The process of claim 1, wherein said solution of said cis-type isomer of said polyene antibiotic comprises a solvent selected from the group consisting of methanol, ethanol, acetonitrile, dimethylformamide, dimethylacedtamide, dimethylsulfoxide, and aqueous mixtures thereof.

* * * * *